United States Patent [19]

Skarnes

[11] Patent Number: 5,789,653
[45] Date of Patent: *Aug. 4, 1998

[54] SECRETORY GENE TRAP

[75] Inventor: William C. Skarnes, Edinburgh, United Kingdom

[73] Assignee: University of Edinburgh, Edinburgh, United Kingdom

[*] Notice: The term of this patent shall not extend beyond the expiration date of Pat. No. 5,767,336.

[21] Appl. No.: 497,076

[22] Filed: Jun. 30, 1995

Related U.S. Application Data

[63] Continuation-in-part of Ser. No. 404,727, Mar. 15, 1995.

[30] Foreign Application Priority Data

Jan. 10, 1995 [GB] United Kingdom ............ 9500423

[51] Int. Cl.$^6$ ............ C12N 5/00; C12N 15/00; C12P 19/34
[52] U.S. Cl. ............ 800/2; 800/DIG. 1; 435/91.1; 435/172.3; 435/320.1; 435/325
[58] Field of Search ............ 435/320.1, 240.2, 435/325, 91.1, 172.3; 800/2, DIG. 1

[56] References Cited

PUBLICATIONS

Molecullar Cloning : A Laboratory Manual, 2nd ed, Sambrook et al, Cold Spring Harbor Laboratory Press, Cold Spring Harbor, NY, 1989, 1.13,1.85–1.86.

*Primary Examiner*—Deborah Crouch
*Attorney, Agent, or Firm*—Richard Aron Osman

[57] ABSTRACT

The invention relates to secretory gene trap vectors and methods of using such vectors to isolate extracellular proteins and to make cells and organisms with mutant secretory genes. The vectors encode a type II transmembrane domain and a secretory lumen -sensitive indicator marker and optionally, a selectable marker and an exon-splice acceptor site. The gene isolation methods involve stably introducing the secretory trap vectors into an endogenous gene whereby the expression of the resultant fusion protein provides a differential expression of the indicator marker depending on whether the endogenous gene provides an N-terminal signal sequence.

12 Claims, 2 Drawing Sheets

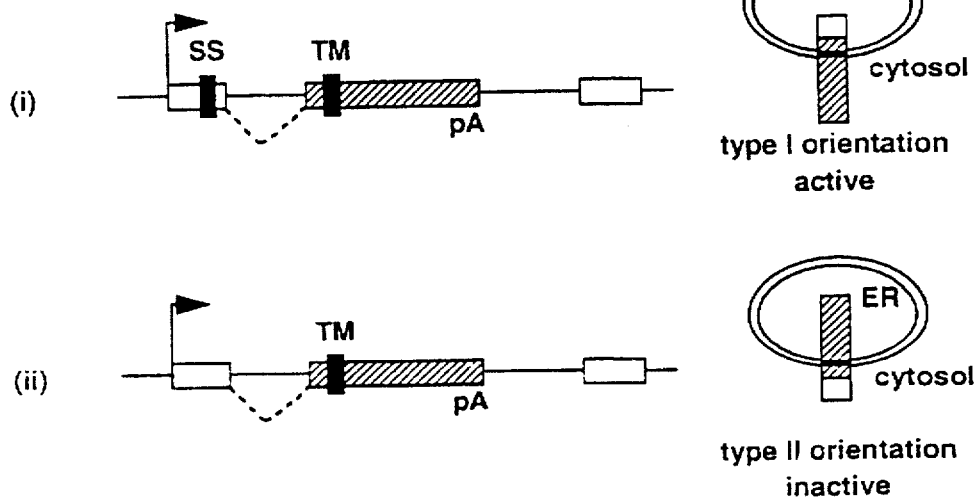

SECRETORY GENE TRAP

This application is a continuation in part of U.S. Ser. No. 08/404,727, filed Mar. 15, 1995, which claims priority from UK application No. 9500423.0.

This invention relates to novel vectors and use thereof for capturing target genes encoding membrane and secreted proteins.

BACKGROUND

Secreted proteins are generally but not exclusively characterised in that they contain an N-terminal extension (or "signal sequence") of roughly 18 to 25 hydrophobic amino acids. This signal sequence directs the translation product to the secretory pathway such that the polypeptide translocates across a cell membrane for export from the cell. For the most part, the signal sequence is proteolytically cleaved from the polypeptide during the secretion process whereby the final secreted product lacks this sequence. Secreted proteins in this class include, for instance, polypeptide hormones and cytokines.

Membrane-spanning proteins generally contain, in addition to a signal sequence, one or more hydrophobic sequences, often of similar size, downstream of the signal sequence. The transmembrane domain prevents further translocation of the polypeptide, so resulting in the production of a protein that spans the membrane. Transmembrane proteins in this class are all oriented in a type I orientation where the N-terminus of the protein is oriented towards the outside of the cell and include, for instance, receptors for polypeptide hormones and receptors for cytokines. There also exist a minor class of membrane spanning proteins that lack an N-terminal signal sequence and these proteins may exist in either a type I or type II orientation (High, 1992). Type II membrane proteins are inserted in the membrane such that the N-terminus remains in the cytosol. The orientation that these proteins adopt is largely determined by the charge differential across the internal transmembrane domain (Hartman, Rappaport and Lodish, 1989).

A variety of expression cloning strategies have been developed over the years to identify secreted and membrane spanning proteins (Simmons, 1993). These strategies rely on cloning random cDNAs into expression vectors and screening transfected cells for the appearance of antigenic determinants on the surface of cells. In a recent embodiment of this technique, the "signal sequence trap" (Tashiro et al., 1993), cDNA fragments encoding an N-terminal signal sequence were identified by assaying for the appearance of a specific antigenic determinant on the surface of transiently transfected cells. Expression cloning systems to identify new secreted or membrane-spanning proteins are technically demanding and generally favour the detection of abundant mRNA species. Moreover, the function and expression profile of genes isolated by these methods cannot be ascertained without considerable additional effort.

"Gene trapping" has been developed to generate random insertional mutations in genes of eukaryotic cells (Gossler et al. 1989, Brenner et al. 1989, Kerr et al. 1989 and Friedrich and Soriano, 1991). Typically such vectors possess structural components which facilitate isolation of vector sequences inserted into transcription units so as to form recombinant sequences and other elements which allow the resulting recombinant sequences to be identified and/or characterised. Thus for example, the known vectors may contains sequence which are commonly associated with eukaryotic structural genes such as for example, splice acceptor sites which occur at the 5' end of all exons and polyadenylation sites which normally follow the final exon. If the vector inserts within an intron in the correct orientation the splice acceptor and polyadenylation sites are utilized to generate a fusion RNA transcript that contains a portion of the target gene spliced to reporter gene sequences of the vector. Other vectors with similar function do not rely on splicing, but instead recombine within coding sequences of the target gene simply as a result of random recombinational events.

Each insertion event that activates expression of the reporter gene theoretically represents insertions that disrupt the normal coding sequences of the target gene to create a mutation. Furthermore, expression of the reporter gene is under the regulatory control of the target gene and thus reporter gene expression should reflect the expression pattern of the target gene (Skarnes et al. 1992). Lastly, a portion of the target gene contained in the RNA fusion transcript may be cloned directly from the fusion transcript or from genomic DNA upstream of the site of insertion (Skarnes et al. 1992, von Melchner et al. 1992, Chen et al. 1994, DeGregori et al. 1994). unction do not rely on splicing, but instead recombine within coding sequences of the target gene simply as a result of random recombinational events.

Gene trapping in mouse embryonic stem (ES) cells has hitherto offered a rapid, but essentially random method to identify and simultaneously mutate genes expressed during mouse development (Skarnes, 1990). There is, however, a need to identify and/or isolate target eukaryotic genes on the basis of various selection criteria. A particular class of genes of interest are those that encode secreted and membrane-spanning proteins.

Gene trap vectors typically contain the β-galactosidase reporter gene. β-galactosidase (β-gal) is a cytosolic enzyme that lacks a signal sequence and transmembrane domain. This reporter has been a particularly useful tool for the expression of gene fusions in bacteria due to the fact β-gal can accommodate large N-terminal fusions without affecting its enzyme activity (Casadaban, Chou & Cohen, 1980). Fusions containing all or portions of secreted molecules has been used to define the requirement for the N-terminal signal sequence to initiate secretion (Benson, Hall & Silhavy, 1985; Silhavy & Beckwith, 1985). However, these fusions fail to be exported from the cell, suggesting that β-gal is not able to cross bacterial membranes. Similarly, the β-gal reporter appears to be incompatible with secretion pathways in eukaryotic cells. In yeast, β-gal fusions containing the signal sequence of the invertase enzyme associate with the membrane fraction of the ER but fail to traverse further along the secretory pathway (Emr et al., 1984). In these examples, β-gal activity is preserved. In contrast, Caenorhabditis elegans, β-gal activity is lost in a fusion that contained the N-terminal signal sequence of a secreted laminin (Fire, Harrison and Dixon, 1990). Including a predicted type I (Hartman et al. 1989) transmembrane domain between the signal sequence and β-gal, restored enzymatic activity to the fusion protein presumably by keeping β-gal in the cytosol.

We have now developed a strategy which solves the problems outlined above and which in its more specific aspects in based on gene trap protocols. A modified gene trap vector, the secretory trap, was engineered such that the activity of the β-gal reporter gene is dependent on the acquisition of a signal sequence from the endogenous gene at the site of vector insertion. Fusions that do not contain a signal sequence fail to activate reporters cannot be ascertained without considerable additional effort.

SUMMARY OF THE INVENTION

Methods and compositions for detecting and/or isolating targeted genes are provided. According to a first aspect of the present invention, there are provided vectors comprising a component which upon insertion into a target eukaryotic gene produces a modified gene which on expression codes for a polypeptide having a first portion of its amino acid sequence encoded by a nucleic acid sequence of the eukaryotic gene and a second portion of its amino acid sequence encoded by a nucleic acid sequence of the vector, characterised in that the vector includes a sequence which confers on the polypeptide a property which is differentially associated with the presence in eukaryotic gene of a nucleic acid sequence coding for an amino acid sequence which results in the said polypeptide being located in a predetermined spatial relationship with structural components of the host cell.

A particularly useful class of vectors according to the invention are ones wherein the vector includes one or more sequences which confer or confers on the polypeptide a property which is differentially associated with the presence in eukaryotic gene of a signal sequence associated with a secreted or membrane-spanning protein. By being "differentially associated" with the presence in the target eukaryotic gene of a nucleic acid sequence coding for an amino acid sequence which results in the chimeric polypeptide being located in a predetermined spatial relationship with structural components of the host cell, the presence or absence of the differentially associated property allows vectors of the invention to distinguish between (1) target eukaryotic genes possessing a nucleic acid sequence coding for an amino acid sequence which results in the chimeric polypeptide being located in a predetermined spatial relationship with structural components of the host cell and (2) target eukaryotic gene which are devoid of a nucleic acid sequence coding for an amino acid sequence which results in the chimeric polypeptide being located in a predetermined spatial relationship with structural components of the host cell. In preferred embodiments of the invention, the vectors of the invention can distinguish between target eukaryotic genes which (1) code for proteins which possess a signal sequence, e.g. secreted proteins and ones which (2) code for proteins which do not possess a signal sequence, e.g. non-secreted proteins.

The aforementioned "conferring" sequences can, for example comprise at least a portion of a membrane-associated protein. In this embodiment, the protein product encoded by a reporter gene element of the vector can be forced to adopt, on integration into a target gene, one of two configurations, depending on whether or not gene includes a signal sequence associated with a secreted or membrane-spanning protein. Thus for example, if gene does code for a secreted or membrane-spanning protein the membrane-associated protein element of the vector sequence can cause a reporter gene product to adopt a configuration in relation to cell components such that the reporter gene product is activated and produces a detectable signal. Alternatively if the vector is incorporated into target gene which does not code for a secreted or membrane-spanning protein, the membrane-associated protein element of the vector sequence will cause reporter gene product to adopt a configuration in relation to cell components such that the reporter gene product is not activated and consequently will not produce a detectable signal.

The membrane protein associated protein element of the vector sequence is preferably a type II transmembrane domain, i.e. a domain which includes a membrane-spanning sequence and any necessary flanking sequences (see below). Thus preferred vectors include a reporter gene and a sequence encoding a type II transmembrane domain, preferably placed N-terminally to the reporter, each mutually arranged so that on expression of the modified gene, detection of reporter polypeptide is dependent upon the eukaryotic gene coding for a secreted protein having a signal sequence, and the reporter is substantially undetectable if the eukaryotic gene codes for a non-secreted protein. The reporter generally provides a characteristic phenotype, e.g. an enzymic activity such as β-galactosidase activity.

The vectors of the invention preferably include a nucleic acid sequence which facilitates insertion of said component into eukaryotic gene. These sequences may for example be (a) sequences associated with elimination of intron sequences from mRNA, such as, for example splice acceptor sequences, or (b) polyadenylation signal sequences. Alternatively, the vector may lack a splice acceptor sequence and thus rely on insertions directly into the coding sequences of genes.

The subject vectors may also include an element allowing selection and/or identification of cells transformed as a result of components of the vector having been inserted into the target eukaryotic gene. Such a selectable element conveys a second property on transformed cells which may be independent of the differentially associated property; for example, a property allowing selection of cells wherein components of the vector have been inserted into the target eukaryotic gene as a result of conferring antibiotic resistance or the ability to survive and/or multiply on a defined medium. Examples of such marker sequences are ones which result in transformed cells being resistant to an antibiotic, for example G418, or having a varied degree of dependence on a growth factor or nutrient. Vectors possessing sequences which result in the chimeric polypeptide possessing both the differentially associated property and a distinct selectable property are especially preferred, though the two properties can result from the same element (e.g. a selectable marker which is differentially active according to a predetermined spatial relationship with structural components of the cell). An example of the former vectors are ones possessing sequences conferring both β-galactosidase (β-gal) and neomycin (neo) phosphotransferase activities on the chimeric protein. The construct βgeo combining sequences conferring both β-galactosidase (β-gal) and neomycin (neo) phosphotransferase activities in a single construct is particularly preferred.

As discussed, the selective inactivation of the differentially associated property in chimeric polypeptides that do not acquire a signal sequence of an endogenous gene depends on the insertion of the chimeric polypeptide in a type II orientation in the membrane of the ER. Suitable type II transmembrane domains are preferably identified empirically, as described below. In addition, the orientation of proteins that contain internal transmembrane domains (signal anchor sequences) but no signal sequence may frequently be predicted from the number of positive charged amino acids within 15 amino acids either side of the transmembrane domain (Hartmann, Rappaport & Lodish, 1989). However, proteins with a predicted type I orientation may be forced into a type II orientation if the N-terminus contains many positively charged amino acids. Such orientation dispositive flanking sequences are readily identified, as shown with CD4, below. In these cases, it is necessary to retain these dispositive flanking sequences to preserve the type II character of the domain. Using these guidelines, transmembrane domains from any of the known type II proteins may be selected for designing new secretory trap vectors; suitable transmembrane domains include those from type II proteins listed by Hartmann, Rappaport & Lodish (1989), for examples, transmembrane domains of human P-glycoprotein, of human transferrin receptor, or of rat Golgi sialyltransferase. Alternatively, synthetic or hybrid type II transmembrane domains may be used.

The invention further provides a method of detecting and/or isolating a target eukaryotic gene encoding a protein which is located in a predetermined spatial relationship with structural components of the host cell which comprises transforming a cell utilising a vector as defined above and detecting the transformed cell by assaying for said property which is differentially associated with the presence in the target eukaryotic gene of a nucleic acid sequence coding for an amino acid sequence which results in said polypeptide being located in a predetermined spatial relationship with structural components of the host cell. In a preferred embodiment, the method is a method for isolating a target eukaryotic gene encoding an extracellular protein, comprising steps: (1) introducing into a plurality of cells a vector encoding a type II transmembrane domain and a lumen-sensitive indicator marker, wherein said indicator marker is oriented 3' relative to said type II transmembrane domain, whereby said vector stably integrates into the genomes of said plurality of cells to form a plurality of transgenic cells, wherein at least cell of said plurality of cells, said vector stable integrates into a gene encoding an extracellular protein having an N-terminal signal sequence; (2) incubating said plurality of cells under conditions wherein said indicator marker is expressed in a preferentially active form as a fusion protein with an N-terminal region of said extracellular protein in said cell or a descendent of said cell, and is unexpressed or expressed in a preferentially inactive form in said plurality of cells not expressing said indicator marker as a fusion protein with an N-terminal region of an extracellular protein having an N-terminal signal sequence; (3) detecting the expression of active indicator marker at said cell or a descendent of said cell; and, (4) isolating from said cell or a descendent of said cell a nucleic acid encoding least an N-terminal region of said extracellular protein.

The vectors of these methods comprise a lumen-sensitive marker, i.e. a marker which is preferentially detectable when not present in a secretory lumen of a cell, e.g. the ER, Golgi, secretory vesicles, etc. For example, the marker may be an enzyme such as galactosidase which is preferentially inactivated in the lumen. An equivalent way of practising the invention is to use a marker which is preferentially detectable when present in the lumen. The important feature is that the marker is differentially detectable depending upon if it is present in or outside the lumen. When the marker is preferentially detectable outside the lumen, the vectors also comprise a type II transmembrane domain as described above. In addition, the vectors may comprise a selectable marker which may be the same or different from the lumen-sensitive marker, as described above.

The vectors may be introduced into the cells by any convenient means. For example, with cells in culture, conventional techniques such transfection (e.g. lipofection, precipitation, electroporation, etc.), microinjection, etc. may be used. For cells within an organism, introduction may be mediated by virus, liposome, or any other convenient technique.

A wide variety of cells may be targeted by the subject secretory trap vectors, including stem cells, pluripotent cells such as zygotes, embryos, ES cells, other stem cells such as lymphoid and myeloid stem cells, neural stem cells, transformed cells such as tumour cells, infected cells, differentiated cells, etc. The cells may be targeted in culture or in vivo.

The vector stably integrates into the genome (i.e. chromatin) of the target cells. Typically, the vector integrates randomly into the genome of a plurality of the cells, though in at least one of the cells, the vector integrates into a gene encoding an endogenous extracellular (i.e. secreted or transmembrane protein) having an N-terminal signal sequence such that the signal sequence is oriented 5' to the vector/insert. Such cell acquires then a mutated allele of the extracellular gene comprising at least a portion of the subject vector encoding the lumen sensitive marker and the type II transmembrane domain.

The cells comprising the stably introduced vector are incubated under conditions whereby the lumen sensitive marker is expressed as in a preferentially detectable form as a fusion protein with an N-terminal region of the extracellular protein, i.e. the fusion protein is preferentially detectable via the marker if the endogenous protein portion includes a functional signal sequence. The incubation conditions are largely determined by the cell type and may include mitotic growth and differentiation of the originally transfected cells.

The marker in preferentially detectable form may be detected in any convenient way. Frequently, the preferential detectability is provided by a change in a marker signal form or intensity such as a color or optical density change. Cells preferentially expressing such a signal presumptively comprise a fusion protein comprising an endogenous signal sequence. The nucleic acid encoding such endogenous signal sequence is then isolated from the cell by conventional methods, typically by cloning the mutant genomic allele or a transcript thereof. In this way, genes encoding known and novel extracellular proteins are obtained. In addition, the subject methods may be modified to obtain a products such as transgenic animals, cell lines, recombinant secretory proteins, etc., some example of which are described below.

DESCRIPTION OF FIGURES

FIG. 1a shows the vectors designed to express CD4/βgeo fusion proteins and summarises the results of transient transfection experiments.

FIG. 1b shows the design of gene trap vectors (pSAβgeo and pGT1.8geo) and the secretory trap vector (pGT1.8TM) and their relative efficiency in stable transfections of ES cells. pSAβgeo contains the minimal adenovirus type 2 major late splice acceptor (SA; open box, intron; shaded box, exon) and the bovine growth hormone polyadenylation signal. The mutation in neo (*) present in pSAβgeo was corrected by replacement of the ClaI (C)/Sph I (S) fragment of βgeo. pGT1.8geo and pGT1.8TM contain the mouse En-2 splice acceptor (Gossler et al., 1989) and SV40 polyadenylation signal but lack a translation initiation signal (ATG). The secretory trap vector pGT1.8TM includes the 0.7 kb PstI/NdeI fragment of CD4 containing the transmembrane domain inserted in-frame with βgeo in pGT1.8geo.

FIG. 1c depicts our model for the selection activation of βgal in the secretory trap vector.

DESCRIPTION OF SPECIFIC EMBODIMENTS

Figure 1D:
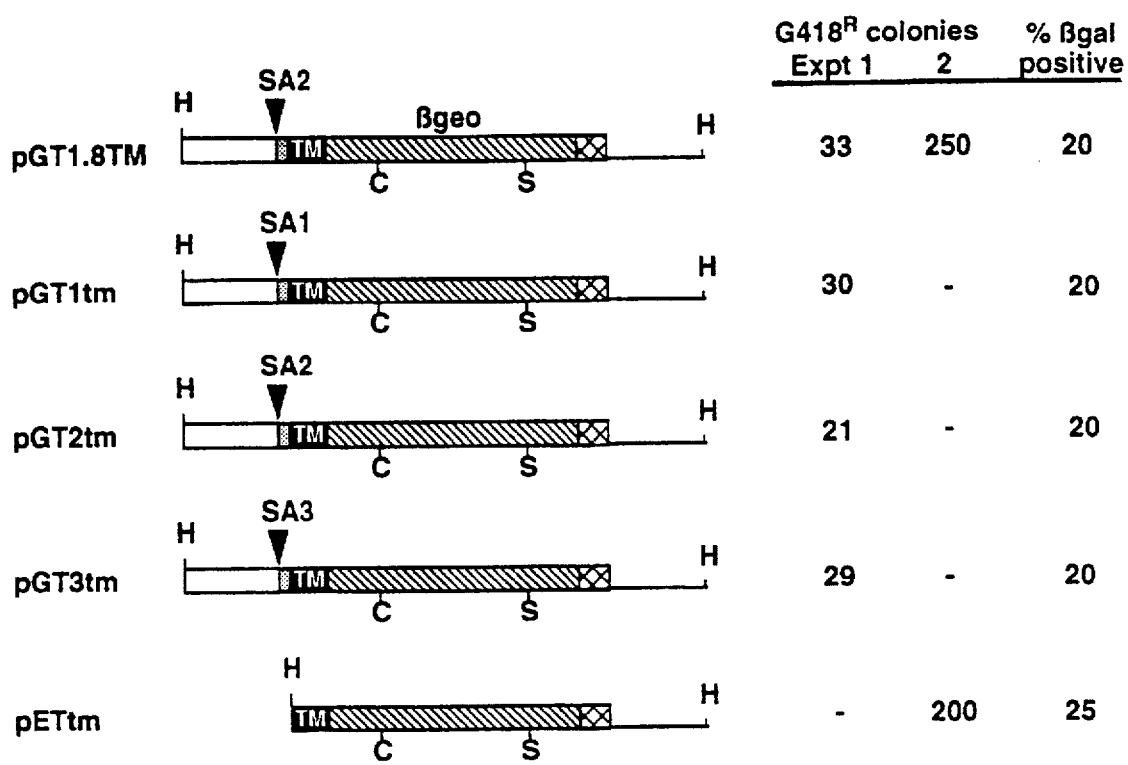
FIG. 1d shows the relative efficiency of secretory trap vectors designed to capture each of the three reading frames and the exon trap design. vectors in each reading frame (pGT1tm to 3tm) were constructed by ExoIII deletion of all but 30 bp of En-2 exon sequences followed by the insertion of Bgl II linkers. The exon trap vector (pETtm) was made by removing the En-2 splice acceptor from pGT1.8TM.

The following experiments and examples are offered by way of illustration and not by way of limitation.

Modified gene trap vectors (which we have termed "secretory trap") were developed which rely on capturing the N-terminal signal sequence of an endogenous gene to generate an active β-galactosidase fusion protein. Using the prototype vector pGT1.8TM (FIG. 1b), insertions were found in the extracellular domains of a novel cadherin, an unc6- related laminin, the sek receptor tyrosine kinase and two receptor-linked protein tyrosine phosphatases, LAR and PTPκ, thus confirming the selective property of the secretory trap vector to detect insertional mutations in genes encoding transmembrane and secreted protein products.

The secretory trap strategy was developed starting from lacZ-based gene trap vectors (Gossler et al., 1989; Brenner et al., 1989; Kerr et al., 1989; Friedrich & Soriano, 1991; Skarnes, Auerbach & Joyner, 1992). These vectors can create N-terminal β-galactosidase (βgal) fusion products which localise to different compartments of the cell, presumably reflecting the acquisition of endogenous protein sequences that act as sorting signals (Skarnes et al., 1992; Burns et al., 1994).

Here, we have exploited the differential sorting of β-gal fusion proteins as a means to capture genes encoding N-terminal signal sequences, genes therefore likely to be expressed on the cell surface.

Materials and Methods Vectors. The βgeo reporter was obtained by replacing the ClaI (unique in lacZ)/SphI (unique in neo) fragment of the gene trap vector pGT1.8 with the ClaI/SphI fragment of pSAβgeo (Friedrich & Soriano, 1991). pGT1.8 is a derivative of pGT4.5 (Gossler et al., 1989) where the 3' En2 sequences were replaced with the 0.2 kb BclI/BamHI SV40 polyA signal. The parental vector pActβgeo contains the 0.5 kb human β-actin promoter (Joyner, Skarnes & Rossant, 1989) linked to the βgeo/SV40 polyA cassette. The start of βgeo translation was engineered to contain a Kozak consensus sequence with unique SalI and NruI sites on either side for generating subsequent fusions. SalI sites were placed at each end of a BalI fragment containing the entire coding region of the rat CD4 cDNA (Clark et al., 1987) A 0.45 kb SalI/KpnI fragment containing the N-terminus of CD4 or a 1.4 kb SalI/NdeI fragment containing the entire CD4 coding region was cloned into SalI/NruI digested pActβgeo to generate pActSSβgeo and pActSSTMβgeo, respectively. The secretory trap vector pGT1.8TM includes the 0.7 kb PstI/NdeI fragment of CD4 containing the transmembrane domain (TM) inserted in-frame with βgeo in pGT1.8geo.

ES cell culture. CGR8 ES cells (a feeder-independent cell line derived from strain 129/Ola mice by J. Nicholas (Mountford et al. 1994) were maintained in Glasgow MEM/BHK12 medium containing 0.23% sodium bicarbonate, 1×MEM essential amino acids, 2 mM glutamine, 1 mM pyruvate, 50 μM β-mercaptoethanol, 10% feotal calf serum (Globepharm), and 100 units/ml DIA/LIF. Transiently transfected cells were obtained by electroporating $10^7$ ES cells with 100 μg plasmid DNA in a volume of 0.8 ml PBS using a BioRAd Gene Pulser set at 250 μF/250 V and cultured for 36 hours on gelatized coverslips prior to analysis. To obtain stable cell lines, between $5\times10^7$ to $10^8$ CGR8 ES cells were electroporated (3 μF/800V) with 150 μg linearised plasmid DNA, $5\times10^6$ cells were plated on 10 cm dishes and colonies were selected in 200 μg/ml Geneticin (GibCo). To assay βgal enzyme activity and protein, ES cells were grown on gelatinized coverslips and stained with X-gal or with polyclonal rabbit αβ-Bgal antiserum and FITC-conjugated donkey α-rabbit IgG (Jackson ImmunoResearch). To permeabilize membranes, cells were treated with 0.5% NP-40 prior to antibody staining.

RNA analysis and RACE cloning. Northern blots and RACE were carried out as previously described (Skarnes et al 1992). Several modifications were incorporated into the 5' RACE procedure used previously (Skarnes, Auerbach & Joyner, 1992): 1) microdialysis (0.025 micron filters, Millipore) was used in place of ethanol precipitations, 2) nested PCR (30 cycles each) was carried out using an anchor primer and a primer specific to CD4 followed by size selection on agarose gels and a second round of PCR with the anchor and the En-2 256 primer and 3) chromospin 400 columns (Clontech) were used to size select XbaI/KpnI-digested PCR products prior to cloning.

Results

To test if βgal fusions that contain an N-terminal signal sequence could be identified by their subcellular distribution, vectors were constructed to express portions of the CD4 type I membrane protein (Clark et al., 1987) fused to βgeo, a chimeric protein that possesses both βgal and neomycin phosphotransferase activities (Friedrich & Soriano, 1991) (FIG. 1a). βgeo fused to the signal sequence of CD4 (pActSSβgeo) accumulated in the endoplasmic reticulum (ER) but lacked Bgal activity. Therefore, translocation of βgeo into the lumen of the ER appeared to abolish βgal enzyme function. βgal activity was restored by including the transmembrane domain of CD4 (pActSSTMβgeo), presumably by keeping βgal in the cytosol. Active protein was associated with the ER and in multiple cytoplasmic inclusions, a pattern only rarely observed in ES colonies obtained with the conventional gene trap vector probably because insertions downstream of both a signal sequence and transmembrane domain of genes encoding membrane spanning proteins are infrequent. Therefore, to identify insertions in both secreted and type I membrane proteins our gene trap vector pGT1.8geo was modified to include the transmembrane domain of CD4 upstream of βgeo (FIG. 1b). Vectors were linearised prior to electroporation at either the Sca I (Sc) site in the plasmid backbone (represented by the line) of pSAβgeo or at the Hind III (H) site at the 5' end of the En-2 intron. The number of G418-resistant colonies obtained in two electroporation experiments (Expt 1: $5\times10^7$ cells; Expt 2: $10^8$ cells) and the proportion that express detectable βgal activity is indicated on the right. With the secretory trap vector pGT1.8TM βgal enzyme activity is restored to any insertion occurring downstream of a signal sequence.

In a pilot experiment, the relative efficiency of our gene trap vector was compared to the original pSAβgeo following electroporation into ES cells. Although pSAβgeo contains a start of translation which is absent in our vectors, fewer G418-resistant colonies were obtained with pSAβgeo than with pGT1.8geo. More importantly, nearly all the colonies derived with pSAβgeo showed high levels of βgal activity, whereas our vector showed a broad range of staining intensities and a greater proportion of βgal negative colonies. Sequence analysis of the pSAβgeo vector revealed a point mutation in neo known to reduce its enzyme activity (Yenofsky, Fine & Pellow, 1991). Therefore, the pSAβgeo vector appears to pre-select for genes expressed at high levels and correction of the neo mutation in our vectors now allows us to access genes expressed at low levels (see below).

Approximately half of the pGT1.8geo colonies express detectable βgal activity and show various subcellular patterns of βgal staining observed previously. In contrast, only 20% of the pGT1.8TM colonies express βgal activity and all display the "secretory" pattern of βgeo activity characteristic of the pActSSTMβgeo fusion. Stable cell lines transfected with pGT1.8TM in most cases showed detectable βgal activity in undifferentiated ES cells however, we occasionally found ES cell lines that exhibited detectable βgal activity only in a subset of differentiated cell types. The reduction in the proportion of βgal-positive colonies and the singular pattern of βgal staining observed with the secretory trap vector suggested that βgal activity is retained only in fusions that contain an N-terminal signal sequence and that βgal activity, but not neo activity, is lost in fusions with proteins that do not possess a signal sequence.

Our data indicate that in the absence of cleavable N-terminal signal sequence, the fusion protein behaves as a type II membrane protein (High, 1992), placing βgeo in the ER lumen where the βgal enzyme is inactive (FIG. 1c). To confirm this, several βgal-negative cell lines were isolated and analysed by immunofluorescence. βgal-negative cells lines were identified from immunodotblots of whole cell lysates using a-βgal antibodies and the ECL detection system (Amersham). From a screen of 48 colonies, three βgal-negative cell lines were recovered and analysed by immunofluorescence. In these lines, the fusion protein was detected on the surface of cells in the absence of detergent permeabilization, indicating a type II orientation of the βgeo fusion protein. In contrast, detergent permeabilization was essential to detect the fusion protein in βgal-positive cell lines, as would be expected for type I membrane proteins.

A model for the observed selective activation of βgal in the secretory trap vector is presented in FIG. 1c. Insertion of pGT1.8TM (hatched box) in genes that contain a signal sequence produce fusion proteins that are inserted in the membrane of the endoplasmic reticulum in a type I configuration. The transmembrane domain of the vector retains βgal in the cytosol where it remains active. Insertion of the vector in genes that lack a signal sequence produce fusion proteins with an internal TM domain. In these fusions, the transmembrane domain acts as a signal anchor sequence (High, 1992) to place βgeo in a type II orientation, exposing βgeo to the lumen of the ER where βgal activity is lost. This dependence of enzyme activity on acquiring an endogenous signal sequence provides a simple screen for insertions into genes that encode N-terminal signal sequences. Further proof for this model has come from cloning several genes associated with several secretory trap insertions.

5' RACE (rapid amplification of cDNA ends) was used to clone a portion of the endogenous gene associated with secretory trap insertions that express detectable βgal activity (Table 1). Northern and RNA dot blot analysis showed that approximately one half (5 of 11 analyzed in this study) of the G418-resistant cell lines fail to properly utilize the splice acceptor and produce fusion transcripts that hybridize with intron sequences of the vector. These insertions presumably do not represent true gene trap events and thus were not analyzed further. Northern blot analysis of six properly-spliced lines detected a unique-sized βgal fusion transcript in each cell line. For these experiments, a Northern blot of 15 μg ES cell RNA was hybridised with lacZ gene and reprobed with a RACE cDNA fragment cloned from the ST534 (LAR) insertion. At least two independent RACE cDNAs were cloned from each cell line. The cDNAs obtained from all cell lines except ST514 detected both the fusion transcript and an endogenous transcript common to all cell lines as shown for the ST534 probe. The ST514 insertion illustrates that genes expressed a very low levels in ES cells can be trapped. In ST514 cultures, βgal activity was observed only in a few differentiated cells and accordingly neither the fusion nor the endogenous transcripts could be detected on Northern blots.

Sequence analysis of the RACE cDNAs in all cases showed the proper use of the splice acceptor and a single open reading frame in-frame with βgeo. One insertion occurred in netrin, a secreted laminin homologous to the unc-6 gene of *C. elegans* (Ishii et al. 1992) recently cloned in the chick (Serafini et al. 1994). The remaining five insertions interrupted the extracellular domains of membrane spanning proteins: a novel cadherin most closely related to the fat tumour suppressor gene of Drosophila (Mahoney et al. 1991), the sek receptor tyrosine kinase (Gilardi-Hebenstreit et al. 1992), the receptor-linked protein tyrosine phosphatase PTPκ (Jiang et al. 1993), and two independent insertions in a second receptor-linked tyrosine phosphatase LAR (Streuli et al. 1988). These results support the prediction that βgal activity is dependent on acquiring an N-terminal signal sequence from the endogenous gene at the site of insertion.

The pattern of βgal expression in embryos derived from insertions in the sek (ST497) and netrin-1 (ST514) genes was very similar to published RNA in situ results for the mouse sek (Nieto et al., 1992) and chick netrin (Kennedy et al., 1994) genes, providing further proof that gene trap vectors accurately report the pattern of endogenous gene expression (Skarnes, Auerbach & Joyner, 1992). For these experiments, chimeric embryos and germline mice were generated by injection of C57B1/6 blastocysts (Skarnes, Auerbach & Joyner, 1992). Embryos at the appropriate stages were dissected, fixed and stained with X-gal as described Beddington et al., 1989). Both insertions in LAR (ST484, 534) exhibited weak, widespread expression in 8.5d embryos. The insertion in PTPκ (ST531) showed βgal expression in endoderm and paraxial mesoderm, highest in newly condensing somites. βgal expression in tissues of adult mice carrying insertions in LAR and PTPκ correlated well with known sites of MRNA expression (Jiang et al., 1993; Longo et al., 1993). Highest levels of βgal activity were found in the lung, mammary gland and brain of ST534 (LAR) mice and in the kidney, brain and liver of ST531 (PTPκ) mice.

ES cell lines containing insertions in the LAR, PTPκ, and sek genes have been transmitted to the germline of mice. Following germline transmission of the PTPκ and LAR insertions, breeding analysis showed that mice homozygous for either insertion are viable and fertile. To confirm that the LAR and PTPκ genes were effectively disrupted, Northern blots of RNA from wild-type and homozygous adult tissues were probed with cDNAs from regions downstream of each insertion site. In Northern blots of 10 μg RNA from wild-type (+/+), heterozygous (±) and homozygous (−/−) lung of ST534 (LAR) and kidney of ST531 (PTPκ) adult mice were hybridized with LAR and PTPκ cDNA sequences 3' to the insertion and reprobed with the ribosomal S12 gene as a loading control. For both mutations, normal full-length transcripts were not detected in homozygous animals.

Because secretory trap insertions generate fusions that in some cases will contain a large portion of the extracellular domain of the target gene, the production of both loss of function and gain of function (i.e., dominant-negative) mutations are possible. However, since the βgeo fusions with LAR and PTPκ include less than 300 amino acids of the extracellular domains of these proteins, these insertions likely represent null mutations. LAR and PTPκ are members of an ever-increasing family of receptor PTP genes (Saito, 1993). The absence of overt phenotypes in LAR and PTPκ mutant mice is likely due to functional overlap between gene family members, as has been observed with targeted mutations in multiple members of the myogenic and Src-family genes (Rudnicli et al. 1993; Stein, Vogel & Soriano, 1994; Lowell, Soriano & Varmus, 1994).

Based on the first six genes identified, the secretory trap shows a preference for large membrane-spanning receptors. The recovery of two independent insertions in LAR further suggests that the current vector design will access a restricted class of genes. The requirement for gene trap vectors to insert in introns of genes is predicted to impose an inherent bias in favour of detecting genes composed of large intronic regions and consequently limit the number of genes accessible with this approach. To access a larger pool of genes, we have constructed vectors in each of the three possible reading frames. Furthermore, to recover insertions in smaller transcription units composed of few or no introns, we developed an "exon trap" version of the vector of that lacks a splice acceptor. The relative efficiencies of secretory trap vectors engineered in all three reading frames and the exon trap vector are given in FIG. 1d. Electroporations of CGR8 ES cells were carried out as described above (Expt 1: 2×10⁷ cells; Expt 2: 10⁸ cells). Each vector yielded similar numbers of G418-resistant colonies, a similar proportion of which exhibit the secretory pattern of βgal activity. With a combination of vectors, one obtains a more representative sampling of the genome that should include both membrane receptors and secreted ligands.

It will be appreciated that in this invention we have shown that the βgeo reporter gene can be modified to contain an N-terminal transmembrane domain. Integration into an endogenous gene encoding an N-terminal signal sequence produces a fusion protein that assumes a type I configuration, keeping βgal in the cytosol where it retains functional enzyme activity (see FIG. 1c (i)). Conversely, if the modified reporter integrates into a gene that does not encode a signal sequence, the hydrophobic transmembrane domain itself is now recognised by the cell as a signal anchor sequence to place the fusion protein in a type II orientation whereupon the βgal enzyme is inactivated (see FIG. 1c (ii)). Therefore, a construct in which βgal or βgeo is prefixed by an N-terminal type II transmembrane domain has a unique property. If the construct integrates into a 'secretory' gene encoding a signal sequence, the βgal remains active. If it integrates into a non-secretory gene, βgal activity is blocked. This permits integrations into secretory genes to be identified by a simple assay (e.g. color change) for reporter gene activity.

TABLE 1

Identification of the endogenous gene associated with six secretory trap insertions.

| cell line | βgal expression[1] ES | diff | transcript size (kb)[2] fusion | endogenous | gene[3] | phenotype[4] | (wt:het:hom) |
|---|---|---|---|---|---|---|---|
| 484 | + | + | 7.5 | 7.5 | LAR (604) | NA | |
| 497 | + | +/− | 6.5 | 7 | sek (439) | ? | |
| 514 | − | +/− | ND | ND | netrin (404) | ? | |
| 519 | − | +/− | >12 | >12 | novel cadherin | NA | |
| 531 | − | +/− | 6.1 | 5.3 | PTPκ (2.88) | viable | (36:57:27) |
| 534 | + | + | 6.0 | 7.5 | LAR (228) | viable | (36:79:25) |

[1]based on X-gal staining of ES cell cultures that contain a subset of spontaneously differentiated (diff) cell types, (+/−) indicates expression in a subset of differentiated cell types.
[2]transcript sizes were determined from Northern blots (FIG. 4 and data not shown). N.D., not detected.
[3]numbers in parentheses indicate the insertion site within the endogenous based on the amino acid sequence of rat LAR (AC L11586), mouse sek (AC S51422), chick netrin 1 (AC L34549), and mouse PTPκ (AC L10106). The Genbank accession number for the novel cadherin is (to be submitted).
[4]based on the recovery of homozygous animals at weaning age in litters from heterozygous intercrosses. (?) phenotype unknown, breeding in progress. NA, not applicable, insertion not yet in germline.

REFERENCES

Beddington, R. S. P et al. *Development* 106, 37–46 (1989);
Benson et al. Ann. Rev. Biochem. 54, 101–134 (1985)
Brenner, D. G., Lin-Chao, S. & Cohen, S. N. *Proc. Nat. Acad. Sci. USA* 86, 5517–5521 (1989).
Burns, N. et al. *Genes Dev.* 8, 1087–1105 (1994).
Casadaban et al. J Bacteriol. 143, 971–980 (1980)
Clark, S. J. et al., *Proc. Nat. Acad. Sci. USA* 84, 1649–1653 (1987).
Emr et al. Mol Cell Biol. 4, 2347–2355 (1984)
Fire et al. Gene 93, 189–198 (1990)
Friedrich, G. & Soriano P. *Genes Dev.* 5, 1513–1523 (1991).
Frohman, M. A., Dush, M. K., & Martin, G. *Proc. Nat. Acad. Sci. USA* 85, 8998–9002 (1988).
Gilardi-Hebenstreit, P. et al. *Oncogene* 7, 2499–2506 (1992).
Gossler, A., Joyner, A. L., Rossant J. & Skarnes, W. C. *Science* 244, 463–465 (1989).
Hartman et al. PNAS 86, 5786–5790 (1989)
High, S. *Bioessays* 14, 535–540 (1992).
Hurtley, S. M. *J. Cell Sci.* 106, 649–655 (1993).
Ishii, N. et al., *Neuron* 9, 873–881 (1992).
Jasin et al. Genes & Development 4, 157–166 (1990).
Jiang, Y.-P. et al. *Mol. Cell. Biol.* 13, 2942–2951 (1993).
Joyner A. L., Skarnes, W. C. & Rossant, J. *Nature* 338, 153–156 (1989).Kennedy, T. E. et al. *Cell* 78, 425–435 (1994).
Kerr, W. G., Nolan, G. P., Serafini, A. T. & Herzenberg, L. A. *Cold Spring Harbor Symp. Quant. Biol.* 54, 767–776 (1989).
Longo, F. M et al. *J. Biol. Chem.* 268, 26503–26511 (1993).
Lowell, C. A., Soriano, P. & Varmus, H. *Genes & Dev.* 8, 387–398 (1994).
Mahoney, P. A. et al. *Cell* 67, 853–868 (1991).
Nieto, M. et al. *Development* 116, 1137–1150 (1992).
Rudnicki, M. A. et al. *Cell* 75, 1351–1359 (1993).
Saito, H. *Semin. Cell Biol.* 4, 379–387 (1993).
Serafini, T. et al. *Cell* 78, 409–424 (1994).
Silhavy et al. *Microbiol Rev.* 49, 398–418 (1985)
Skarnes, W. C. *Biotechnology.* 8, 827–831 (1990).
Skarnes, W. C., Auerbach, A. & Joyner, A. L. *Genes Dev.* 6, 903–918 (1992).

Stein, P. L., Vogel, H. & Soriano, P. *Genes & Dev.* 8, 1999–2007 (1994).
Stewart, C. L. *Methods Enzymol.* 225, 823–855 (1993).
Streuli, M. et al. *J. Exp. Med.* 168, 1523–1530 (1988).
Tashiro et al. *Science* 261, 600–603 (1993).
Yenofsky, R. L., Fine, M. & Pellow, J. W. *Proc. Nat. Acad. Sci. USA* 87, 3435–3439 (1991).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A vector comprising a DNA sequence encoding a first fusion protein comprising a secretory lumen-sensitive indicator marker and a type II secretory protein transmembrane domain positioned N-terminally of the marker, wherein upon transfer into a cell and stable integration of the DNA sequence into a gene encoding an extracellular protein having an N-terminal signal sequence, the marker is expressed in an active form as a second fusion protein with an N-terminal region of the extracellular protein.

2. A vector according to claim 1, wherein the vector further encodes a selectable marker.

3. An isolated cell comprising a vector according to claim 1, wherein the DNA sequence is stably integrated into a gene of the cell encoding an extracellular protein having an N-terminal signal sequence, and the marker is expressed in an active form as a second fusion protein with an N-terminal region of the extracellular protein.

4. A transgenic mouse comprising a vector according to claim 1, wherein the DNA sequence is stably integrated into a gene of the mouse encoding an extracellular protein having an N-terminal signal sequence, and the marker is expressed in an active form as a second fusion protein with an N-terminal region of the extracellular protein.

5. A method for isolating a target eukaryotic gene encoding an extracellular protein, the method comprising the steps;

a) introducing into a cell in vitro a vector comprising a DNA sequence encoding a first fusion protein comprising a secretory lumen-sensitive indicator marker and a type II secretory protein transmembrane domain positioned N-terminally of the marker, wherein upon transfer into the cell, the DNA sequence stably integrates into a gene encoding an extracellular protein having an N-terminal signal sequence;

b) incubating the cell in vitro under conditions wherein the indicator marker is expressed by the cell or descendant of the cell in a preferentially active form as a second fusion protein with an N-terminal region of the extracellular protein;

c) detecting the presence of the preferentially active form of the indicator marker, wherein the presence of the preferentially active form of the indicator marker indicates that the gene encodes an extracellular protein;

d) isolating the gene encoding the extracellular protein.

6. A method according to claim 5, wherein the vector further encodes a selectable marker.

7. A method according to claim 5, wherein the cell is an embryonic stem cell.

8. A method according to claim 5, wherein the preferentially active form is a detectable mount of catalytic activity.

9. A method for making a transgenic cell comprising a mutation in a gene encoding an extracellular protein, said method comprising steps:

(a) introducing into a cell in vitro a vector comprising a DNA sequence encoding a first fusion protein comprising a secretory lumen-sensitive indicator marker and a type II secretory protein transmembrane domain positioned N-terminally of the marker, whereby upon transfer into the cell, the DNA sequence stably integrates into a gene encoding an extracellular protein having an N-terminal signal sequence;

(b) incubating the cell in vitro under conditions wherein said indicator marker is expressed by the cell or descendant of the cell in a preferentially active form as a second fusion protein with an N-terminal region of the extracellular protein (c) detecting the expression of the preferentially active form of the indicator marker, wherein the expression of the preferentially active form of the indicator marker indicates the presence of the second fusion protein, and the presence of the second fusion protein indicates that the cell is a transgenic cell comprising a mutation in a gene encoding an extracellular protein.

10. A method according to claim 9, wherein the vector further encodes a selectable marker.

11. A method according to claim 9, wherein the cell is a pluripotent cell.

12. A method according to claim 9, wherein the preferentially active form is a detectable amount of a catalytic activity.

* * * * *